United States Patent [19]

Subramanyam et al.

[11] Patent Number: 5,602,087
[45] Date of Patent: Feb. 11, 1997

[54] COMPOSITION

[75] Inventors: Ravi Subramanyam, North Brunswick; Ben Gu, East Brunswick, both of N.J.

[73] Assignee: Colgate-Palmolive Company, New York, N.Y.

[21] Appl. No.: 284,857

[22] Filed: Aug. 2, 1994

[51] Int. Cl.$^6$ ........................................... C11D 1/14
[52] U.S. Cl. ..................... 510/127; 510/152; 510/156; 562/111
[58] Field of Search .................................. 252/554, 549, 252/555; 260/400, 513

[56] References Cited

U.S. PATENT DOCUMENTS

| | | | |
|---|---|---|---|
| 1,916,776 | 7/1933 | Steindorf et al. | 260/400 |
| 2,093,576 | 9/1934 | Segesseman | 260/106 |
| 2,535,677 | 12/1950 | Hollander et al. | 260/513 |
| 2,806,044 | 9/1957 | Weil et al. | 260/400 |
| 2,923,724 | 2/1960 | Anderson et al. | 260/400 |
| 2,999,871 | 9/1961 | Schenck | 260/400 |
| 3,879,309 | 4/1975 | Gatti et al. | 252/117 |
| 4,515,721 | 5/1985 | Losin et al. | 260/400 |
| 4,554,098 | 11/1985 | Klish et al. | 252/547 |
| 5,310,508 | 5/1994 | Sasramanyam et al. | 252/549 |
| 5,417,852 | 5/1995 | Subramenyam et al. | 252/554 |

FOREIGN PATENT DOCUMENTS

| | | |
|---|---|---|
| 88199787 | 2/1990 | Japan . |
| 90118701 | 1/1992 | Japan . |

OTHER PUBLICATIONS

Dahanayake, et al., "Relationship of Structure to Properties of Surfactants", J. of Physical Chemistry, vol. 90, No. 11, 1986 (2413–2418).

Carmona, et al. "Synthesis and performance of linear monoisomeric ethylene oxide sulphonate surfactants", J. of Dispersion Science and Technology, vol. 4, No. 4, 1983 (361–370).

No. 101:74769 Synthesis and Performance of Linear Monoisomeric ethylene Oxide Sulphonate Surfactants, Carmona, I., Schecter, R. S.; Wade, W. H.; Weevasouriya, U: J. of Dispersion Sci. and Techn. vol. 4 pp. 361–370 1983.

*Primary Examiner*—Paul Lieberman
*Assistant Examiner*—Necholus Ogden
*Attorney, Agent, or Firm*—Martin Barancik

[57] ABSTRACT

A composition comprising a compound of the formula $ROCH_2CH_2SO_3^-X^+$ wherein R is alkyl or alkenyl of eight to twenty two carbon atoms, inclusive or a mixture thereof and X is an alkali metal, alkaline earth metal, ammonium or substituted ammonium in combination with a soap or additional surfactant and moisture.

4 Claims, No Drawings

COMPOSITION

BACKGROUND OF THE INVENTION

New surfactants are continually being discovered for usage in compositions requiring surfactant activity. Of particular interest are surfactants for personal cleansing compositions, shampoos, body washes, shower gels, make up removal, cosmetics, laundry detergents, bath and kitchen cleaning of hard surfaces and the like. Various synthetic surfactants have become quite successful over the years of usage such as sodium cococyl isethionate (SCI), alkyl glyceryl ether sulfonates (AGES), cocoylmonoglyceride sulfate (CMGS) and the like.

A new surfactant has now been discovered which will be useful in the above named consumer product areas, particularly in personal cleansing, shampoos, body washes and shower gels. It is characterized by relative simplicity in structure, a desirable mildness and an unusually stable structure when exposed to conditions which bring about instability to ester bonds.

SUMMARY OF THE INVENTION

In accordance with the invention there is a composition comprising a compound of the formula.

$$ROCH_2CH_2SO_3^-X^+ \qquad \text{FIG. I}$$

(1)

where R is alkyl or alkenyl of eight to twenty two carbon atoms inclusive or mixtures thereof and X is an alkali metal, alkaline earth metal, ammonium or substituted ammonium compound in combination with a soap or other surfactant and moisture.

A further aspect of the invention is the method of preparing a compound of FIG. I. Significant yields of (1) are obtained by reacting in an organic solvent a long chain alcohol, ROH, with a halogenated ethene sulfonate salt Y CH$_2$CH$_2$SO$_3$X or a long chain halide, RY, with an isethionate salt, HOCH$_2$CH$_2$SO$_3$X wherein X and R are defined as above and Y is chloro or bromo, preferably bromo.

DETAILED DESCRIPTION OF THE INVENTION

The R group in the compound is preferably 10 to 20 carbon atoms in length. Although branching can be present in the group it is preferred to be normal. Alkyl is preferred over an unsaturated, alkenyl, group. There can be up to 20 wt %, preferably up to 10 wt % alkenyl grouping present as a mixture with the alkyl as a further preferred mode.

With respect to the X grouping the alkali metal is preferably sodium or potassium, the alkaline earth metal is preferably magnesium or calcium. The ammonium type compound are preferably the hydroxy substituted materials such as triethanolamine. Sodium, potassium, ammonium and triethanolamine are most preferred.

These compounds are prepared in good yield through the reaction of a fatty alcohol ROH (2) with a bromethene sulfonate salt (3) wherein X is the salt moiety to form the alkyl ethane sulfonate salt of formula 1. Another reaction sequence is to react a fatty bromo compound RBr (4) with an isethionate salt (5) wherein X is the salt moiety to form the compound (1). The reaction is run in the presence of a base such as sodium hydroxide or potassium hydroxide which inter alia helps scavenge the hydrogen halide formed in the reaction as well as an organic solvent. The organic solvent can be any organic solvent which solubilizes the reactants and in which the product is less soluble. Examples of solvents include dimethylsulfoxide, tetrahydrofuran or dichloromethane, preferably dimethyl sulfoxide. The reaction scheme is shown below.

ROH + BrCH$_2$CH$_2$SO$_3$Na + KOH  FIG. II (2)    (3)

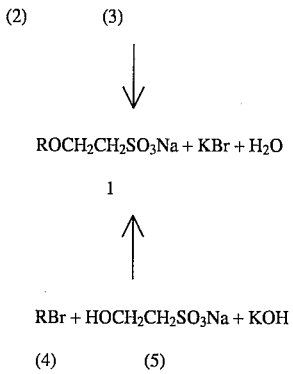

ROCH$_2$CH$_2$SO$_3$Na + KBr + H$_2$O

1

RBr + HOCH$_2$CH$_2$SO$_3$Na + KOH (4)    (5)

Suitable catalysts which can be employed include potassium hydroxide, tetrafluoroboric acid, mercury oxide, and bis-acetylacetonate nickel. Generally the reaction is preferably performed for an extended period of time. Temperatures of from about 25° C. to the reflux and stability termination temperature of the system can be employed. Preferably the temperature is about 50° C. to 90° C. The time of the reaction is dependent upon the catalyst, if present, and the temperature can be employed.

The compound of the inventive composition can be isolated and/or purified by separating the solid material from the organic solvent, dimethylsulfoxide, adding an alcohol such as butanol and water to the solid, separating the organic layer therefrom and then recrystallizing from butanol. Further purification can be achieved by adding water to the solid (crystals) and then recrystallizing.

The novel compositions of the invention are useful in the above-mentioned surfactant applications in any of a variety of formulations such as solid and liquid and can take various forms such as a bar (personal or laundry), aqueous liquid, organic based liquid, mousse, gel and the like and can be combined with a soap, other synthetic surfactant, detergent extender, structural filler, colorant, preservative, chelating agent, antibacterial agent, emollient, fragrance, and any other type of material found in applications of the nature described. The soap which can be employed include any long chain alkyl carboxylate salt such as 8 to 22 carbon atoms alkyl, preferably 10 to 20 carbon atoms alkyl. The salt form is employed. Any other surfactant can also be present such as sulfate, sulfonate alpha olefin sulfonates, isethionates such as SCI, taurates, sulfosuccinate, phosphates, glycinates, amphoteric surfactants such as betaines, sulfobetaines and the like and nonionic surfactants such as alkanolamide, alkylpolyglycosides and all those surfactants, in general, mentioned in U.S. Pat. No. 5,139,781, column 5, line 35 to column 11, line 46, incorporated by reference. The compound of the invention can be present in the composition in quantities of from about 1 to 99 wt % preferably 3 to 90 wt %. The soap or additional surfactants can be present in from about 5 to 90 wt %, preferably about 7 to 50 wt %. The moisture present (water) can be at least 4 wt % of the composition. Generally it will not be above about 12 wt % of the composition.

Below are examples of the invention. Those examples are intended to be illustrative of the invention and are not intended to limit the broad inventive concept. The numbers under reactant refer to the materials of FIG. II

| Example | Reactant | Temp °C. | Time/Hrs | Yield % |
|---|---|---|---|---|
| 1 | 2[a] + 3 | 80 | 3 | 54 |
| 2 | 2[b] + 3 | 85 | 2.5 | 24 |
| 3 | 2[b] + 3 | 85 | 5 | 70 |
| 4 | 4[c] + 5 | 85 | 5 | 24 |

[a] R is 12 and 13 carbon atom normal alkyl
[b] R is 14 and 15 carbon atom normal alkyl
[c] R is 12 carbon atom normal alkyl Potassium hydroxide is present in all of these reactions as well.

These compounds were tested in the in vitro collagen swelling test system, a well known test method as described in Subramanyam et al. U.S. Pat. No. 5,310,508.

The results of the collagen swelling tests are shown below:

| Sample 1% Solution | Collagen - Swelling μl water/mg film |
|---|---|
| SCI | 10.40 ± 0.13 |
| Compound 1[a] | 13.11 ± 0.54 |
| Compound 1[b] | 9.12 ± 0.15 |
| SCI[c] | 12.84 ± 0.28 |

[a] X is sodium, R is normal alkyl of 12 and 13 carbon atoms.
[b] X is sodium, R is normal alkyl of 14 and 15 carbon atoms.
[c] Sodium dodecyl isethionate.

Generally, the longer the hydrophobic portion of the molecule in the long chain salts, the milder to the skin is the surfactant. In the cocoyl grouping, 12 and 14 carbon atom chains constitute the majority wt % of the R groups in SCI. The above data demonstrates that the compounds of the invention are very similar in mildness to SCI when R groups of appropriate length are employed.

However, the compounds of this invention have clear advantages in stability over the ester of the art, particularly the most relevant and structurally closely related SCI molecules, as shown by the decomposition data shown below. Each number represents the quantity of SCI decomposed at the particular conditions.

DECOMPOSITION OF SCI UNDER VARIOUS CONDITIONS

I. Aging of SCI aqueous solutions at room temperature and measurement of decomposition of SCI as wt %.

| Time | SCI | SCI/Soap (⅓) |
|---|---|---|
| 5 h. | −0.21% | −1.53% |
| 24 h | −1.30% | −5.56% |
| 1 week | −5.06% | −27.03% |

II. Aging of SCI in Combar process. (1:3 SCI/Soap) at elevated temperature and measurement of decomposition of SCI as wt %.

| | 15.2% SCI | 11.6% SCI |
|---|---|---|
| Storage at 150° F. | | |
| 4 h | −1.3% | −4.1% |
| 8 h | −3.5% | −6.5% |
| 16 h | −5.4% | −7.0% |
| 24 h | −7.5% | −8.1% |
| Storage at 190° F. | | |
| 4 h | −10.2% | −11.7% |
| 8 h | −14.8% | −15.2% |
| 16 h | −26.2% | −28.69% |
| 24 h | −31.5% | −60.8% |
| Combar Dried Drying at 320° F. (to make chip) | | |
| 5 min | −1.6% | −7.0% |
| 10 min | −5.8% | −21.1% |
| Drying at 340° F. (to make chip) | | |
| 5 min | −3.4% | −11.6% |

III. SCI in Combar (19% SCI) aging study

| Room Temperature | | 110° F. |
|---|---|---|
| 1 month | −2.9% | −9.6% |
| 2 months | −4.5% | −13.4% |

Each of these above studies of decomposition under hydrolyzing conditions was repeated using the compounds of FIG. I, where X is sodium and R is alkyl of 12 and 13 carbon atoms or 14 and 15 carbon atoms.

No decomposition was observed.

The compounds of the invention were stable. Therefore a distinct and significant advantage in personal care compositions is present with compounds of the inventive composition.

We claim:

1. A solid cleansing composition comprising
   a. about 3 to 90 wt. % of a compound of the formula $ROCH_2CH_2SO_3^-X^+$ wherein R is alkyl or alkenyl of eight to twenty two carbon atoms, inclusive or a mixture thereof and X is an alkali metal, alkaline earth metal, ammonium or substituted ammonium in combination with
   b. about 7 to 50 wt. % of a soap or synthetic surfactant selected from the group consisting of anionic surfactants other than a, nonionic surfactants and amphoteric surfactants and
   c. about 4 to 12 wt. % of moisture.

2. The composition in accordance with claim 1 wherein R is 10 to 20 carbon atoms and X is sodium, potassium, ammonium or substituted ammonium.

3. The composition in accordance with claim 2 wherein R is alkyl and X is sodium or substituted ammonium.

4. The composition in accordance with claim 3 wherein R is normal and X is sodium.

\* \* \* \* \*